US012156636B2

(12) United States Patent
Hatano et al.

(10) Patent No.: US 12,156,636 B2
(45) Date of Patent: Dec. 3, 2024

(54) ENDOSCOPE, GROUNDING METHOD AND METHOD FOR GROUNDING DISTAL END PORTION OF ENDOSCOPE

(71) Applicant: OLYMPUS CORPORATION, Tokyo (JP)

(72) Inventors: Keisuke Hatano, Fuchu (JP); Takuya Ariyoshi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 498 days.

(21) Appl. No.: 17/398,393

(22) Filed: Aug. 10, 2021

(65) Prior Publication Data
US 2021/0361144 A1    Nov. 25, 2021

Related U.S. Application Data

(63) Continuation-in-part of application No. PCT/JP2019/005599, filed on Feb. 15, 2019.

(51) Int. Cl.
*A61B 1/00*    (2006.01)
(52) U.S. Cl.
CPC ........ *A61B 1/0011* (2013.01); *A61B 1/00009* (2013.01); *A61B 1/00087* (2013.01); *A61B 1/00124* (2013.01)
(58) Field of Classification Search
CPC .............. A61B 1/0011; A61B 1/00009; A61B 1/00087; A61B 1/00124; A61B 1/00096; A61B 1/051; A61B 1/0008; A61B 1/00114; G02B 23/2484
See application file for complete search history.

(56) References Cited

U.S. PATENT DOCUMENTS

| 5,607,429 A | * | 3/1997 | Hayano | B21F 15/00 |
| | | | | 606/103 |
| 2008/0297922 A1 | * | 12/2008 | Lule | H02K 41/0356 |
| | | | | 348/345 |
| 2013/0050457 A1 | * | 2/2013 | Murayama | A61B 1/00124 |
| | | | | 348/75 |

FOREIGN PATENT DOCUMENTS

| JP | 2007-007227 A | 1/2007 |
| JP | 2013-198566 A | 10/2013 |
| JP | 2015-16240 A | 1/2015 |

(Continued)

OTHER PUBLICATIONS

International Search Report dated Mar. 12, 2019 issued in PCT/JP2019/005599.

*Primary Examiner* — Aaron B Fairchild
(74) *Attorney, Agent, or Firm* — Scully, Scott, Murphy & Presser, P.C.

(57) ABSTRACT

An endoscope includes a frame component provided at a distal end portion of an insertion portion, an exterior member with conductivity in which the frame component fits, an imaging unit fixed to the frame component and configured to pick up an image, a conductive part provided in the imaging unit, an electrical connection part, a first end portion of which is connected to the conductive part, a neighboring part of a second end portion on an opposite side of the first end portion of which is sandwiched and fixed between an outer surface of the frame component and an inner surface of the exterior member and configured to electrically connect the conductive part and the exterior member, and an opening provided in the exterior member and configured to expose part of the frame component and cut an extra portion of the electrical connection part during assembly.

20 Claims, 18 Drawing Sheets

(56) References Cited

FOREIGN PATENT DOCUMENTS

| | | | |
|---|---|---|---|
| JP | 2015016240 A | * | 1/2015 |
| WO | 2012/124526 A1 | | 9/2012 |
| WO | 2020/166070 A1 | | 8/2020 |

* cited by examiner

ENDOSCOPE, GROUNDING METHOD AND METHOD FOR GROUNDING DISTAL END PORTION OF ENDOSCOPE

CROSS REFERENCE TO RELATED APPLICATION

This application is a continuation-in-part application of PCT/JP2019/005599 filed on Feb. 15, 2019, the entire contents of which are incorporated herein by this reference.

BACKGROUND OF THE INVENTION

1. Field of the Invention

The present invention relates to an endoscope with an imaging unit mounted on a non-conductive frame component provided at a distal end portion of an insertion portion, a grounding method and a method for grounding a distal end portion of the endoscope.

2. Description of the Related Art

As is well known, endoscopes are widely used for observation, treatment or the like of a living body (inside of a body cavity) or inspection, repair or the like of an inside of industrial plant equipment. Such endoscopes are provided with insertion portions for being inserted into bent conduits.

As such an endoscope, a configuration with an imaging unit provided at a distal end portion of the insertion portion is known. In order to prevent static electricity, high frequency current or the like applied to the distal end portion from flowing through the imaging unit and causing a defect, the endoscope needs to allow the static electricity, high frequency current or the like to escape to the ground (GND) of the apparatus.

For example, regarding an endoscope, Japanese Patent Application Laid-Open Publication No. 2013-198566 discloses a configuration of an endoscope with a conductive part of an imaging unit provided at an insulating distal end rigid portion and an elastic member electrically connected to a distal end piece, which is a metal member connected to the GND.

SUMMARY OF THE INVENTION

An endoscope according to an aspect of the present invention includes a frame component provided at a distal end portion of an insertion portion, an exterior member with conductivity in which the frame component fits, an imaging unit fixed to the frame component and configured to pick up an image, a lens frame with conductivity provided in the imaging unit, a wire, a first end portion of which is connected to the lens frame, a neighboring part of a second end portion on an opposite side of the first end portion of which is sandwiched and fixed between an outer surface of the frame component and an inner surface of the exterior member and configured to electrically connect the lens frame and the exterior member, and an opening provided in the exterior member and configured to expose part of the frame component and cut the wire during assembly.

A grounding method according to another aspect of the present invention includes inserting a wire into an opening of an exterior member with conductivity, fitting a frame component into the exterior member, sandwiching and fixing the wire between an outer surface of the frame component and an inner surface of the exterior member, and cutting an extended extra portion of the wire by a cutting portion provided in the opening and a cutting tool.

A method for grounding a distal end portion of an endoscope according to a further aspect of the present invention includes inserting an end portion of a wire electrically connected to a lens frame provided in an imaging unit into an opening of an exterior member with conductivity including the imaging unit, fitting a frame component into the exterior member, sandwiching and fixing a neighboring part of an end portion of the wire between an outer surface of the frame component and an inner surface of the exterior member and cutting an extended extra portion of the wire by a cutting portion provided in the opening and a cutting tool.

DETAILED DESCRIPTION OF THE PREFERRED EMBODIMENTS

Here, an endoscope, which is the present invention, will be described as an example. Note that in the following description, drawings based on each embodiment are schematic ones and a thickness-width relationship among components and thickness ratios among the components are different from the actual relationships and ratios, and there are cases where dimensional relationships and ratios differ among drawings.

The endoscope in the following configuration description is an endoscope of which insertion portion has a small diameter, such as a bronchoscope or a urinary endoscope. However, the endoscope is not limited such an endoscope, but the invention is also applicable to a so-called flexible endoscope, an insertion portion of which is flexible to be inserted into an upper or lower digestive organ or a so-called rigid endoscope used for surgery, an insertion portion of which is rigid.

Hereinafter, an endoscope according to an aspect of the present invention will be described based on the accompanying drawings.

Figure 1:
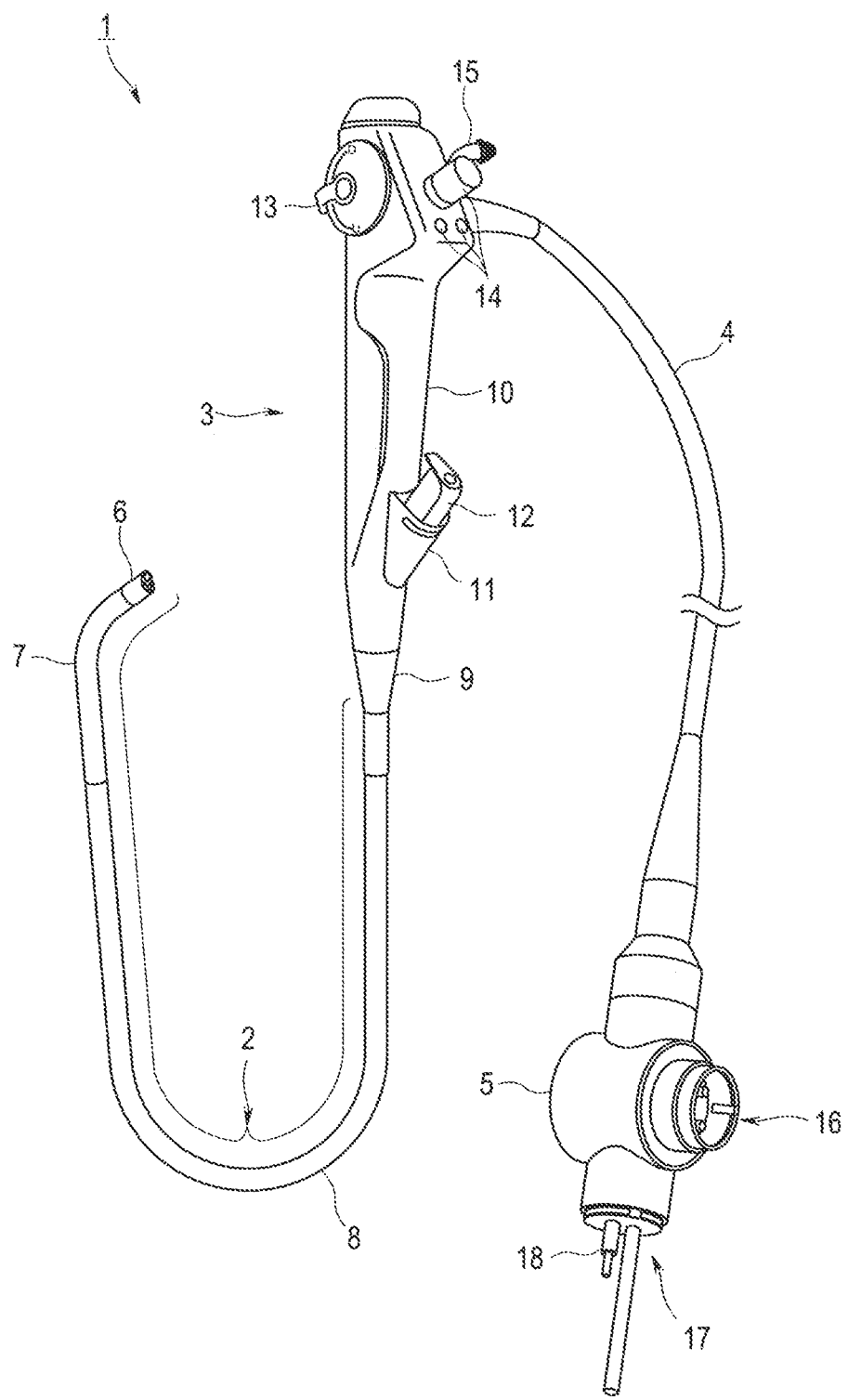
FIG. 1 is a diagram illustrating an appearance of an endoscope according to one aspect of the present invention.

As illustrated in FIG. 1, an endoscope 1, which is an electronic endoscope of the present embodiment, is mainly constructed of an insertion portion 2 formed in an elongated tubular shape, an operation portion 3 connected to a proximal end of the insertion portion 2, a universal cord 4, which is an endoscope cable that extends from the operation portion 3, an endoscope connector 5 disposed at a distal end of the universal cord 4, and the like.

The insertion portion 2 is a flexible tubular member formed by connecting a distal end portion 6, a bending portion 7 and a flexible tube portion 8 in this order from a distal end side. Of these components, the distal end portion 6 accommodates and disposes an imaging unit, which is an image pickup apparatus incorporating image pickup means, which will be described later, and illumination means or the like.

The bending portion 7 is a mechanical part configured to allow the insertion portion 2 to be actively bent in two directions, up and down (UP-DOWN) by rotating operation of a bending lever 13 among the operation members of the operation portion 3.

Note that the bending portion 7 is not limited to a type of bending portion that can be actively bent in two directions, up and down, but may be a type of bending portion that can be bent in four directions including left and right directions in addition to the up and down directions (in all directions around the axis, UP-DOWN/LEFT-RIGHT through up-down, left-right operations) or may be a type of bending portion that can be bent only in one (UP) direction or may be a type of bending portion that simply bends passively without having any mechanism to actively bend by the bending lever 13.

The flexible tube portion 8 is a tubular member formed with flexibility so as to be passively made flexible. In addition to a treatment instrument insertion channel, to be described later, a signal cable bundle, to be described later, extending from an image pickup apparatus incorporated in the distal end portion 6 and further extending from the operation portion 3 to the inside of the universal cord 4, and a light guide bundle, to be described later, which guides illumination light from a light source apparatus and causes the illumination light to be emitted from the distal end portion 6 are inserted through the flexible tube portion 8 (none of the above-described components is shown here).

The operation portion 3 is constructed of a bend preventing portion 9 provided on a distal end side and connected to the flexible tube portion 8 by covering a proximal end of the flexible tube portion 8, a grasping portion 10 connected to the bend preventing portion 9 and configured to be grasped by hand when the user uses the endoscope 1, operation means for operating various endoscope functions provided on an outer surface of the grasping portion 10, a treatment instrument insertion portion 11 and a suction valve 15 and the like.

Examples of the operation means provided in the operation portion 3 include the bending lever 13 that performs bending operation of the bending portion 7 and a plurality of operation members 14 that perform operations corresponding to air/water feeding operation and suction operation, image pickup means, illumination means or the like.

The treatment instrument insertion portion 11 is a component provided with a treatment instrument insertion port through which various treatment instruments (not shown) are inserted and configured to communicate with the treatment instrument insertion channel (not shown) inside the operation portion 3 via a branching member.

The treatment instrument insertion portion 11 is provided with a forceps plug 12, which is a lid member to open/close the treatment instrument insertion port and configured to be attachable/detachable (replaceable) to/from the treatment instrument insertion portion 11. Note that the treatment instrument insertion channel is configured to communicate also with the suction valve 15 by the branching member inside the operation portion 3.

The universal cord 4 is a composite cable through which a signal cable bundle and a light guide bundle that transmits illumination light from a light source apparatus (not shown), which extend from the distal end portion 6 of the insertion portion 2 through the insertion portion 2 to the operation portion 3, are inserted.

The endoscope connector 5 includes, on a side surface thereof, an electric connector portion 16 to which a signal cable for connection with a video processor (not shown) as an external device is connected. The endoscope connector 5 further includes a light source connector portion 17 at which a light guide bundle, which will be described later, and an electric cable (not shown) are connected for connection with the light source apparatus as an external device, and an air/water feeding plug 18 to connect an air/water feeding tube (not shown) from an air/water feeding apparatus (not shown) as an external device or the like.

Here, a configuration of the distal end portion of the insertion portion 2 of the endoscope 1 of the present embodiment will be described based on FIG. 2 and FIG. 3. Note that description of the well-known configuration of the insertion portion 2 is omitted.

Figure 2:
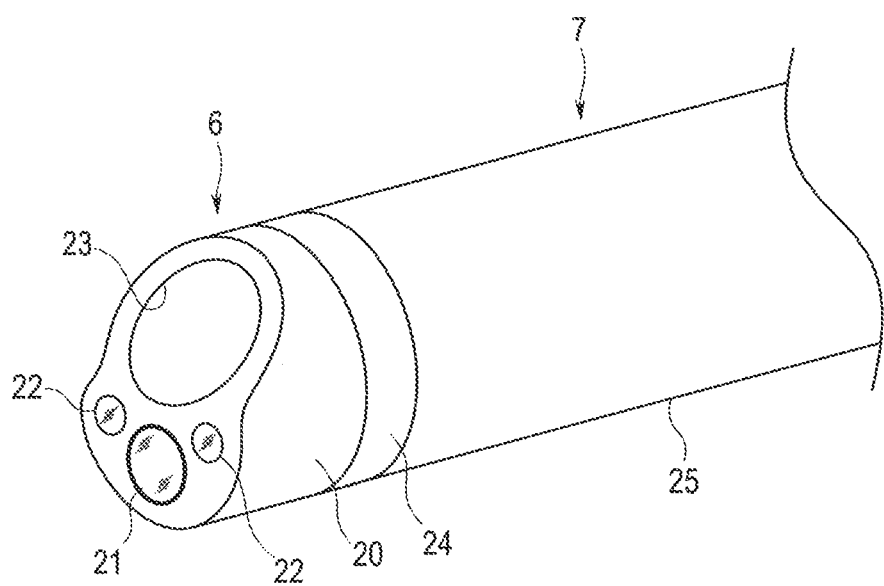
FIG. 2 is a perspective view illustrating a configuration of a distal end portion of an insertion portion of the endoscope according to the one aspect of the present invention.

As illustrated in FIG. 2, the distal end portion 6 of the insertion portion 2 is provided with a distal end rigid portion 20, which is a frame component of an insulating non-conductive substantially columnar block body provided with an observation window 21, illumination windows 22 and a channel opening portion 23. The distal end rigid portion 20 is covered with curved rubber 25 from the middle to the proximal end side and the distal end of the curved rubber 25 is fixed by a thread winding adhesive part 24.

Figure 3:
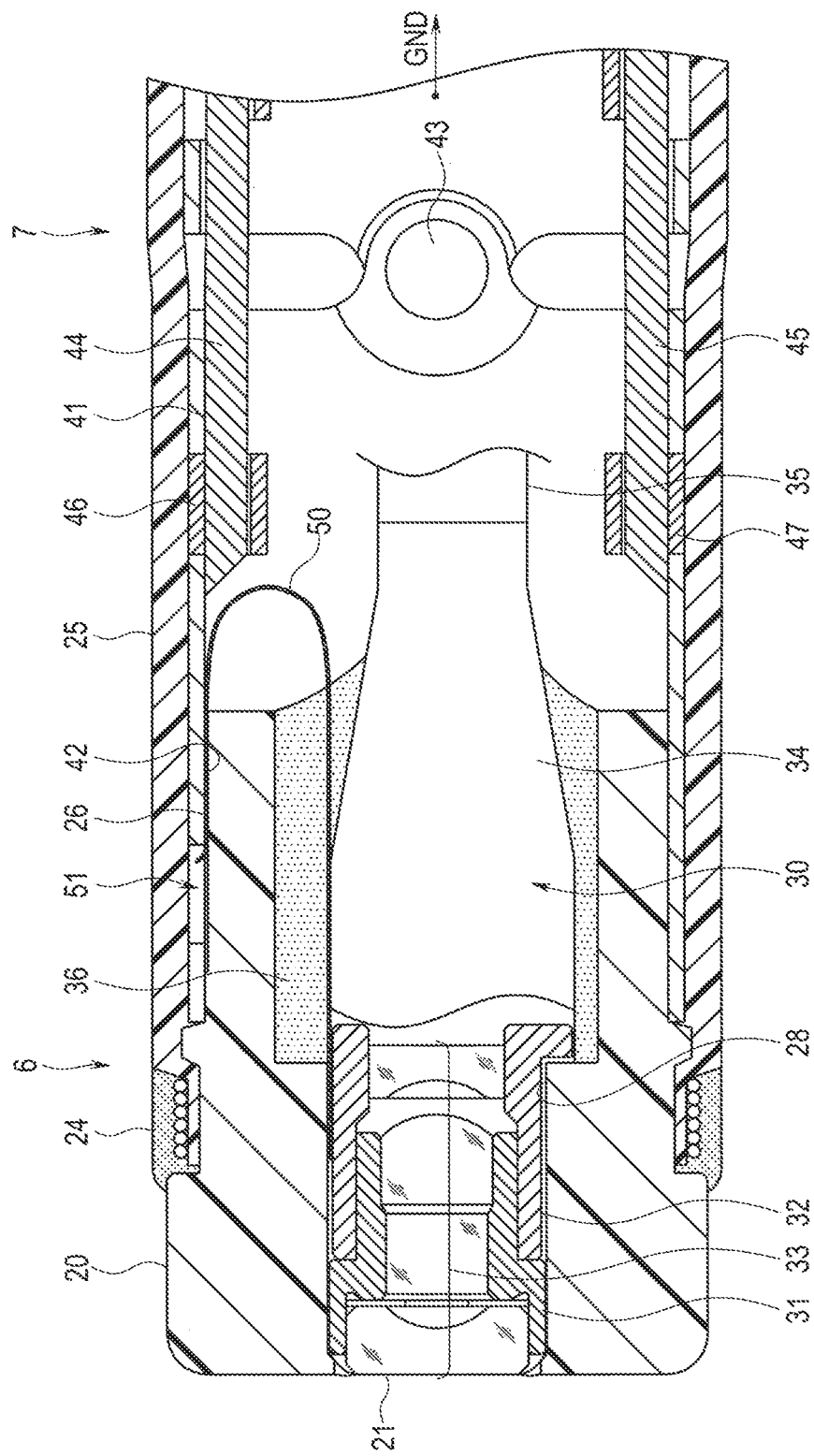
FIG. 3 is a cross-sectional view illustrating a configuration of the distal end portion of the insertion portion of the endoscope according to the one aspect of the present invention.

At the distal end portion 6, as illustrated in FIG. 3, an imaging unit 30 is fitted in a fitting hole 28 formed in the distal end rigid portion 20. The imaging unit 30 is fixed to the distal end rigid portion 20 with a filler 36 such as an adhesive.

The imaging unit 30 includes two lens frames 31 and 32, which are conductive parts made of conductive metals or the like configured to hold an objective lens group 33 including the observation window 21. The imaging unit 30 also includes a thermal contraction tube 34 that covers an element frame (not shown) provided with a solid image pickup device such as CCD or CMOS and a drive circuit board together with a proximal end outer peripheral portion of the lens frame 32 on the proximal end side.

An image pickup cable 35 extends from the thermal contraction tube 34 on the proximal end side. Note that the inside of the thermal contraction tube 34 is filled with an adhesive or the like for watertightness.

A distal end as one end of a jumper wire 50 as an electrical connection part is electrically connected to the lens frames 31 and 32 of the imaging unit 30 with solder or the like. A proximal end as another end of the jumper wire 50 is electrically connected to a most distal end bending piece 41, which is a conductive annular exterior member, externally fitted to an outer peripheral portion 26 on the proximal end side of the distal end rigid portion 20.

This allows conduction so that a current (charge) applied to the lens frames 31 and 32 flows to the jumper wire 50 and the bending piece 41.

The proximal end portion of the jumper wire 50 is held by being sandwiched between the outer peripheral portion 26, which is an outer surface of the distal end rigid portion 20 and an inner surface 42 of the most distal end bending piece 41. In this way, the jumper wire 50 is electrically conducted to the bending piece 41 and the lens frames 31 and 32 of the imaging unit 30 are electrically connected via the jumper wire 50.

Note that the bending piece 41 is made up of a plurality of pieces connected together and axially supported by a pivotally supporting part 43 so as to be rotatable with each other. Bending operation wires 44 and 45 are pulled/relaxed by the bending lever 13 operating the plurality of bending pieces 41.

This causes the plurality of bending pieces 41 to rotate around the pivotally supporting part 43, and the bending portion 7 is thereby bent. Note that the bending operation wires 44 and 45 are fixed to or inserted into or held to wire guides 46 provided on the inner surface side of the plurality of bending pieces 41.

The plurality of bending pieces 41 are each electrically conducted and connected so that a most proximal end bending piece 41 is electrically conducted to a metal braid (not shown) of the flexible tube portion 8. Note that the metal braid of the flexible tube portion 8 is also electrically conducted to the endoscope connector 5 via the operation portion 3 and the universal cord 4.

The endoscope connector 5 is connected to an external device, and a patient ground (GND) is electrically conducted to the imaging unit 30.

Figure 4:
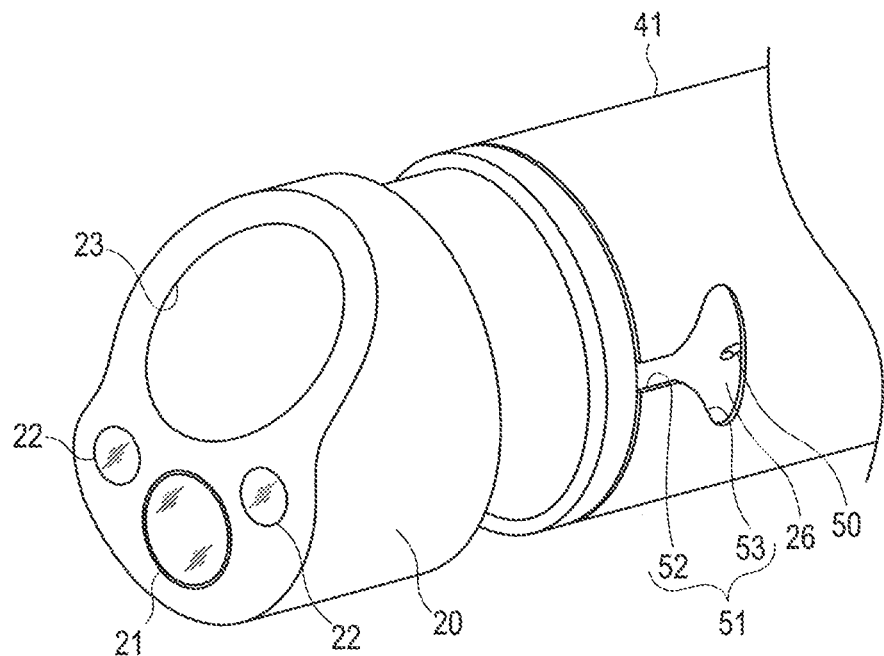
FIG. 4 is a perspective view illustrating a distal end rigid portion fitted in a most distal end bending piece of the endoscope according to the one aspect of the present invention.

The most distal end bending piece 41 in which the distal end rigid portion 20 fits has an opening 51, which is a conductive part cut hole part, part of which is cut out, from an end portion on the distal end side on which a distal end opening portion 47 (see FIG. 6) is provided to the proximal end side as illustrated in FIG. 4. The opening 51 exposes part of the outer circumferential surface of the distal end rigid portion 20.

Figure 5:
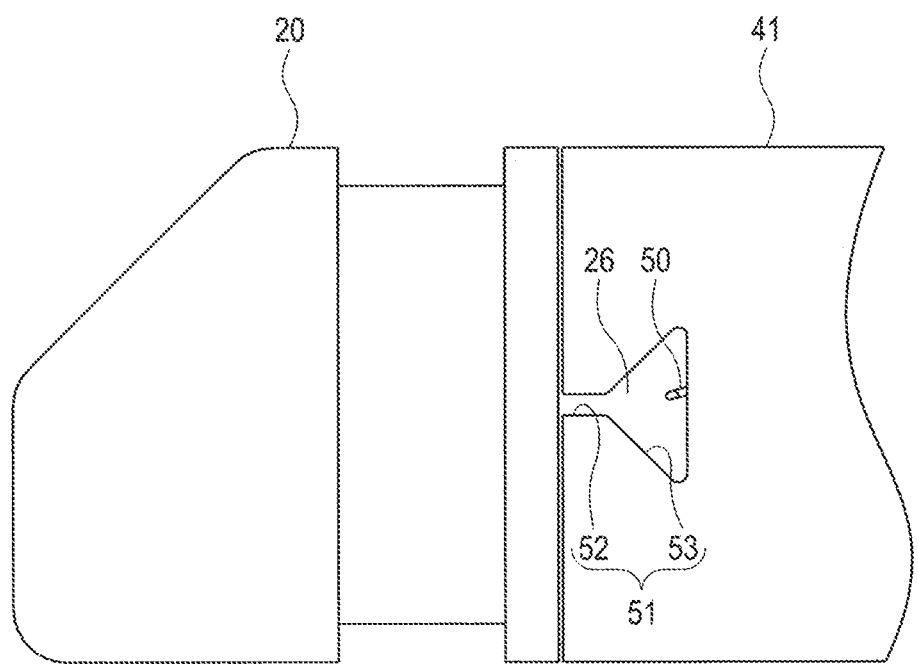
FIG. 5 is a side view illustrating the distal end rigid portion fitted in the most distal end bending piece of the endoscope according to the one aspect of the present invention.

As illustrated in FIG. 5, the opening 51 includes a linear groove portion 52 cut out from the distal end opening portion 47 at an end portion of the bending piece 41 to the proximal end side and a triangular conductive part cut portion 53 that communicates with the groove portion 52.

Here, a configuration in which the distal end rigid portion 20 is fitted in the most distal end bending piece 41 and the jumper wire 50 that extends out of the opening 51 is cut will be described.

Figure 6:
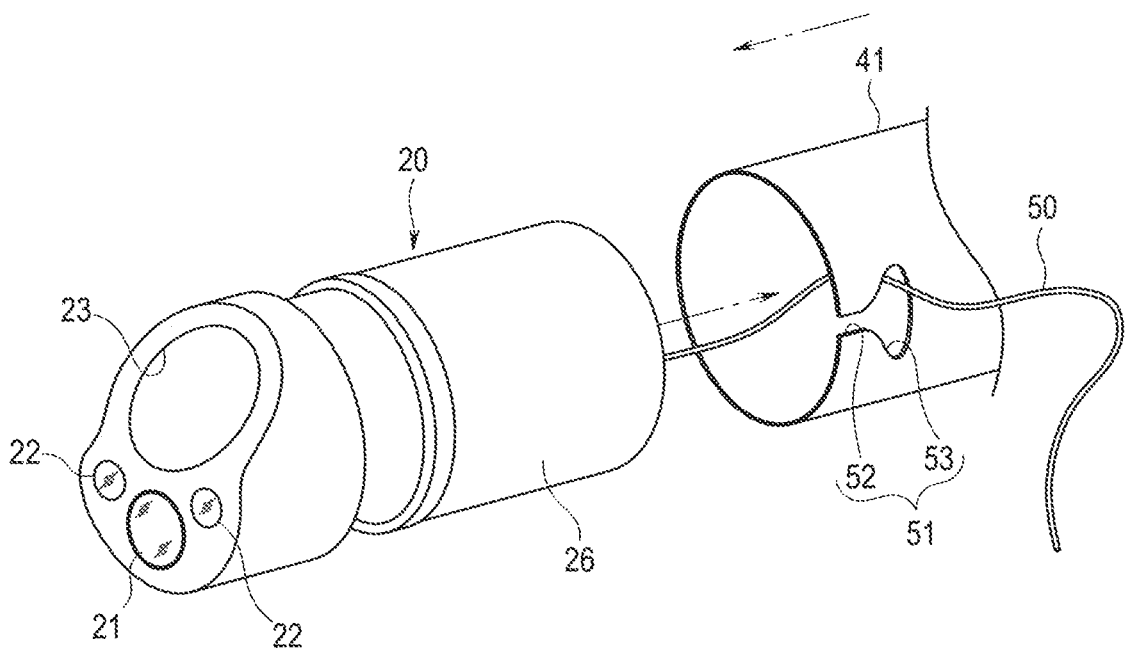
FIG. 6 is an exploded perspective view illustrating the distal end rigid portion fitted in the most distal end bending piece of the endoscope according to the one aspect of the present invention.

When the distal end rigid portion 20 is fitted in the most distal end bending piece 41, as illustrated in FIG. 6, the jumper wire 50 is passed from the groove portion 52 of the opening 51 of the bending piece 41 into the conductive part cut portion 53.

Note that since the jumper wire 50 can be passed into the opening 51 of the bending piece 41, the groove portion 52 that communicates so as to connect the distal end opening portion 47 of the bending piece 41 need not always be connected to the opening 51.

Figure 7:
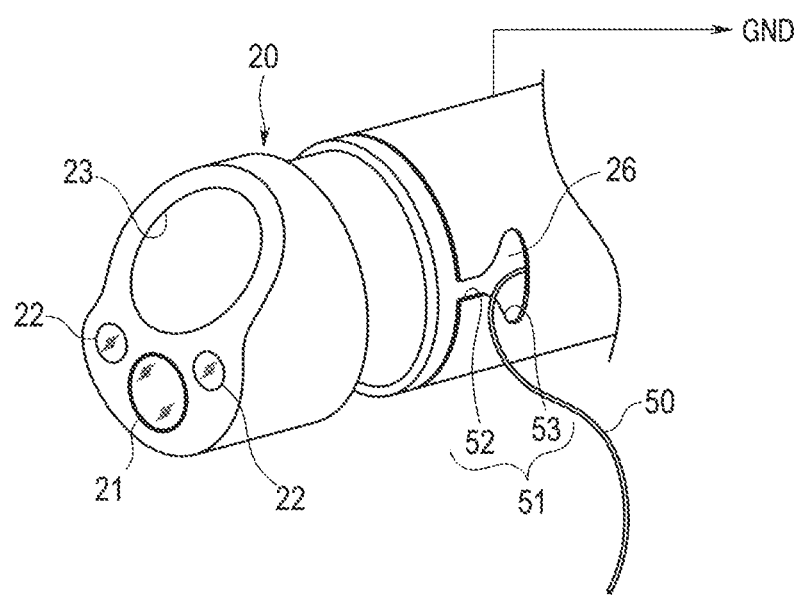
FIG. 7 is a perspective view illustrating a state in which the distal end rigid portion is fitted in the most distal end bending piece and the jumper wire extends out of an opening of the endoscope according to the one aspect of the present invention.

As illustrated in FIG. 7, the distal end rigid portion 20 is fitted in the most distal end bending piece 41. At this time, the jumper wire 50 is sandwiched and fixed between the outer peripheral portion 26, which is an outer surface of the distal end rigid portion 20 and the inner surface 42 of the most distal end bending piece 41, and extends out of the conductive part cut portion 53 of the opening 51.

Figure 8:
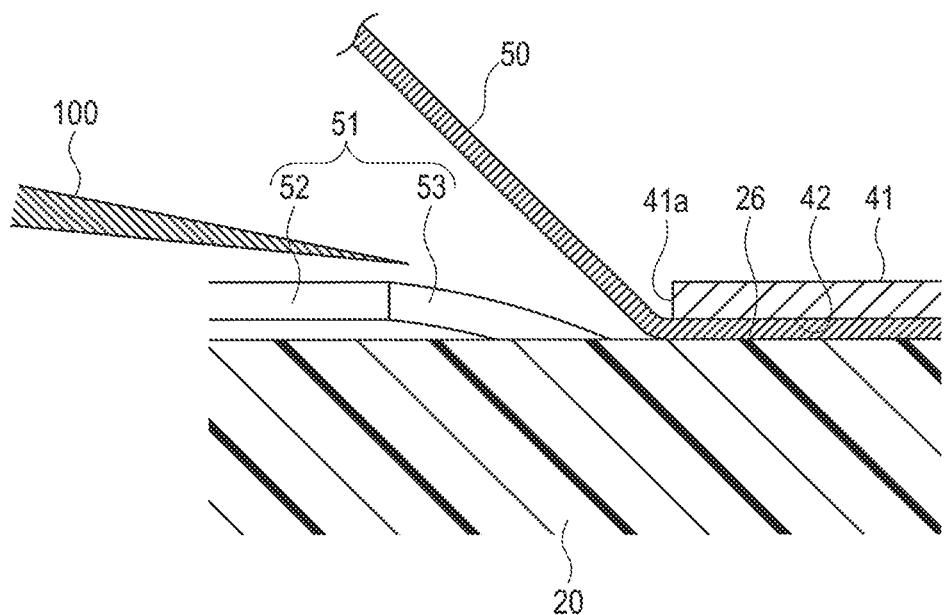
FIG. 8 is a partial cross-sectional view illustrating a state before cutting the jumper wire extending out of the opening of the endoscope according to the one aspect of the present invention.
Figure 9:
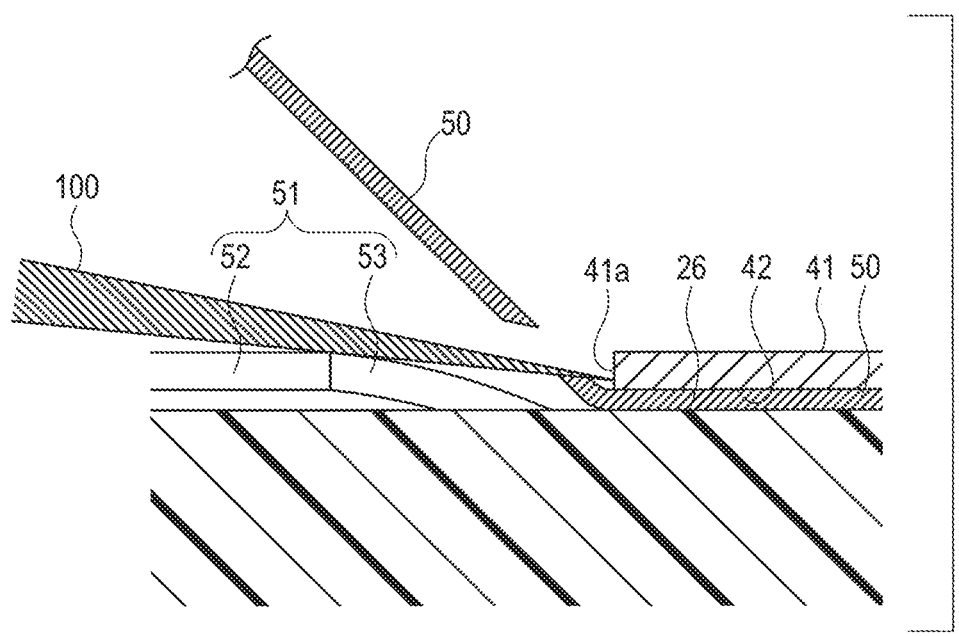
FIG. 9 is a partial cross-sectional view illustrating a state in which the jumper wire extending out of the opening is cut, of the endoscope according to the one aspect of the present invention.

As illustrated in FIG. 8 and FIG. 9, an extra portion of the jumper wire 50 that extends out of the conductive part cut portion 53 is cut using a cutting tool 100 such as a design knife so that the jumper wire 50 fits in the conductive part cut portion 53.

At this time, the cutting tool 100 is guided along the outer surface of the bending piece 41 and directed toward an end face 41a that forms the conductive part cut portion 53 to cut the jumper wire 50. In other words, the jumper wire 50 is cut with the blade of the cutting tool 100 contacting the end face 41a.

An end portion on the proximal end side of the cut jumper wire 50 is fitted in the conductive part cut portion 53 of the opening 51 and cut so that the cut jumper wire does not protrude from the outer surface of the bending piece 41.

Figure 10:
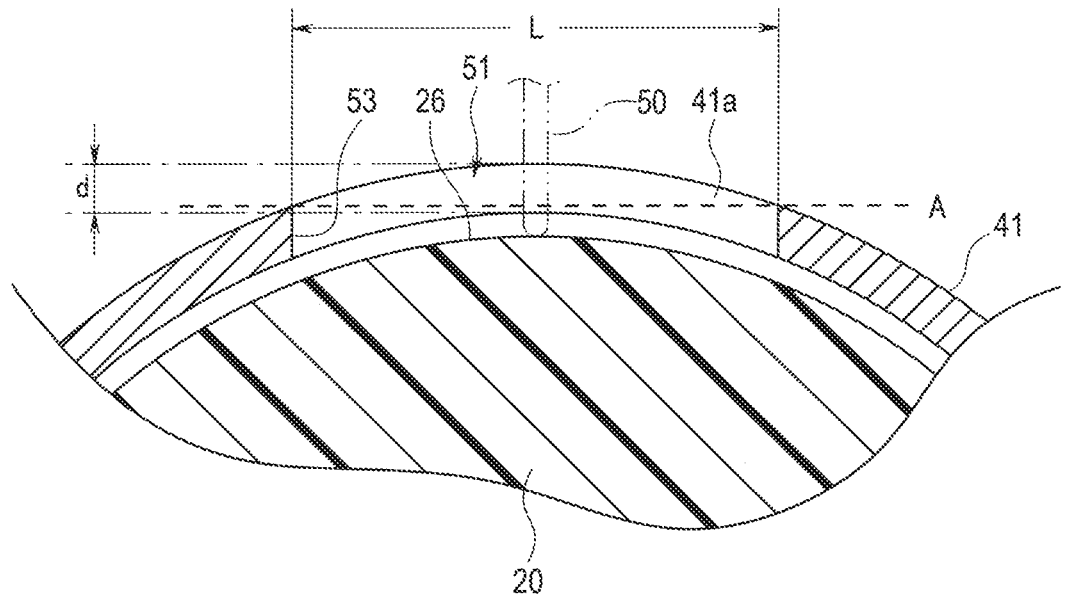
FIG. 10 is a partial cross-sectional view illustrating the distal end rigid portion fitted in the most distal end bending piece and describing a configuration of the opening of the endoscope according to the one aspect of the present invention.

In other words, a length L of the conductive part cut portion 53 of the opening 51 in the annular bending piece 41 in a direction orthogonal to the axis (central axis) of the distal end rigid portion 20 and the bending piece 41 is set so that the blade of the cutting tool 100 is fitted within a thickness d as illustrated in FIG. 10.

Thus, a cutting line A along which the cutting tool 100 cuts the jumper wire 50 along the outer surface of the bending piece 41 is fitted within the thickness d of the bending piece 41, and it is thereby possible to cut the jumper wire 50 so that the jumper wire 50 does not protrude from the outer surface of the bending piece 41.

In addition, the blade of the cutting tool 100 never contacts the distal end rigid portion 20, and so it is also possible to prevent the distal end rigid portion 20 from being shaved.

The endoscope 1 configured as described above is configured so that when the distal end rigid portion 20 is fitted in the most distal end bending piece 41, a neighboring portion of the end portion on the proximal end side of the jumper wire 50 connected to the lens frames 31 and 32, which are conductive parts of the imaging unit 30, is sandwiched between the distal end rigid portion 20 and the bending piece 41 and can be electrically connected to the conductive bending piece 41 easily and reliably.

Thus, in the endoscope 1, even when a high frequency current or the like generated from static electricity, a treatment instrument or the like is applied to the distal end portion 6 of the insertion portion 2 where the non-conductive distal end rigid portion 20 is provided and flows to the lens frames 31 and 32 of the imaging unit 30, the high frequency current or the like is dropped from the jumper wire 50 to the ground (GND) via the bending piece 41. In other words, a charge generated in the distal end portion 6 flows to the lens frames 31 and 32, and is leaked from the jumper wire 50 to the ground via the bending piece 41. Therefore, the imaging unit 30 of the endoscope 1 can prevent defects caused by static electricity, high frequency current or the like.

Furthermore, since the jumper wire 50 is cut by the cutting tool 100 so that the jumper wire 50 does not protrude from the outer surface of the bending piece 41, the curved rubber 25 that covers the bending piece 41 is not damaged.

As described so far, the endoscope 1 has a simple structure in which in order to ground the imaging unit 30, a neighboring portion at one end of the jumper wire 50, which is a conductive wire is sandwiched between the distal end rigid portion 20, which is a distal end frame component that insulates the imaging unit 30 from outside and the bending piece 41, which is an exterior member connected to the ground (GND).

Furthermore, the jumper wire 50 is provided so that the distal end of the jumper wire 50, which is a conductive wire, is fitted within the thickness d of the bending piece 41, which provides a structure that prevents the end portion of the jumper wire 50 from damaging the curved rubber 25, which is a rubber outer shell.

Note that the distal end rigid portion 20 is preferably non-conductive, but without being limited to this, the distal end rigid portion 20 may be conductive as well.

First Modification

Figure 11:
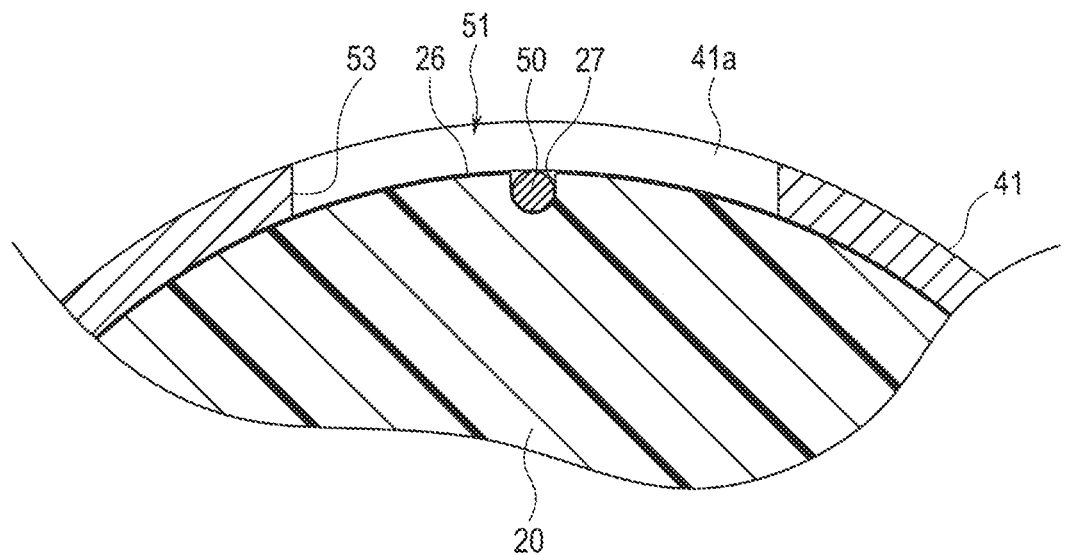
FIG. 11 relates to a first modification of the endoscope according to the one aspect of the present invention and is a partial cross-sectional view illustrating the distal end rigid portion including a concave portion in which the jumper wire is disposed fitted in the most distal end bending piece.

As illustrated in FIG. 11, the distal end rigid portion 20 may also be provided with a linear concave portion 27 configured to dispose the jumper wire 50 on an outer peripheral portion. It is thereby possible to fit the distal end rigid portion 20 in the bending piece 41 with high accuracy.

Second Modification

Figure 12:
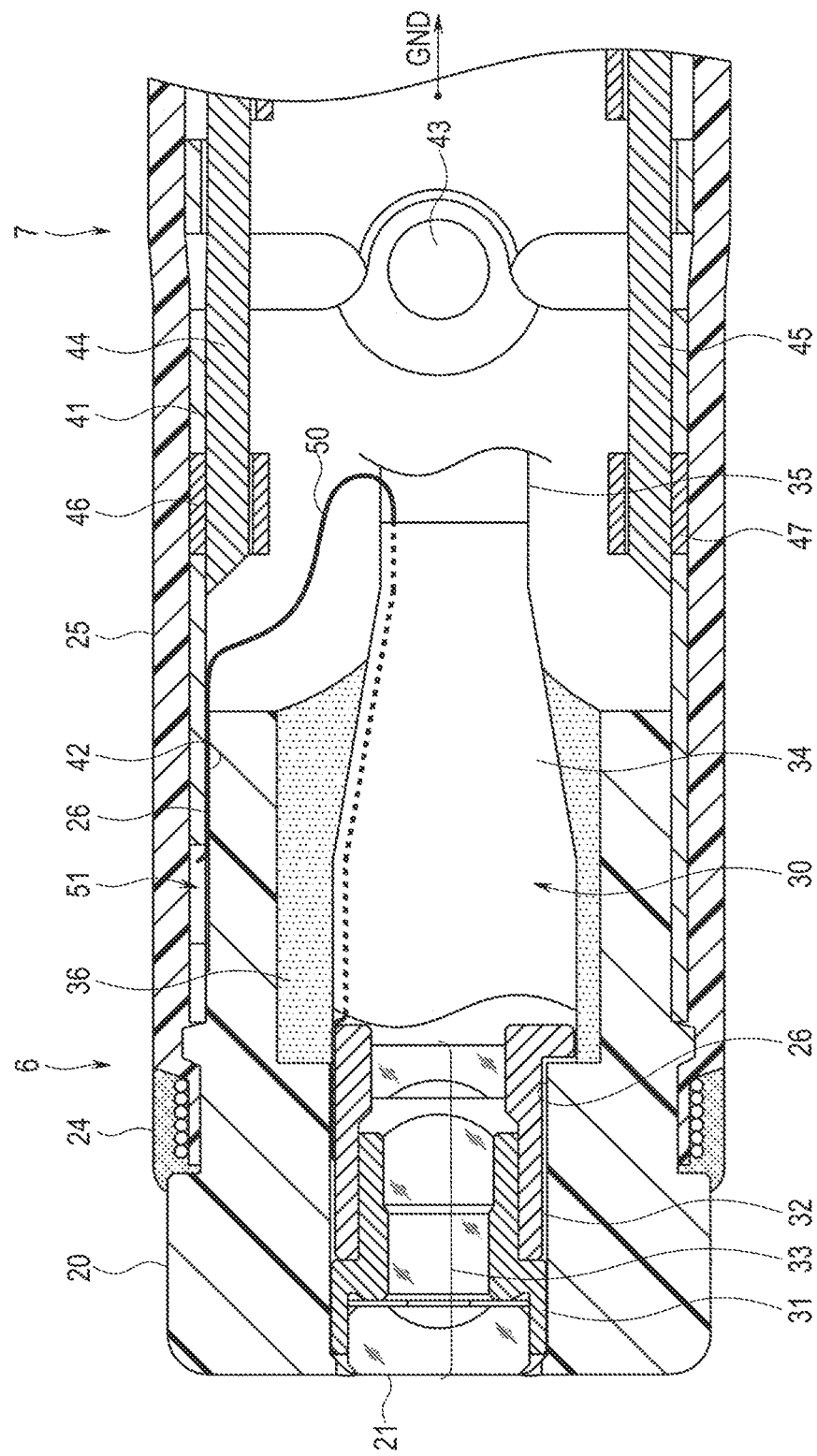
FIG. 12 relates to a second modification of the endoscope according to the one aspect of the present invention and is a cross-sectional view illustrating a configuration of the distal end portion of the insertion portion.

As illustrated in FIG. 12, the jumper wire 50 may be provided in the thermal contraction tube 34 and configured to extend out of the proximal end of the thermal contraction tube 34.

Third Modification

Figure 13:
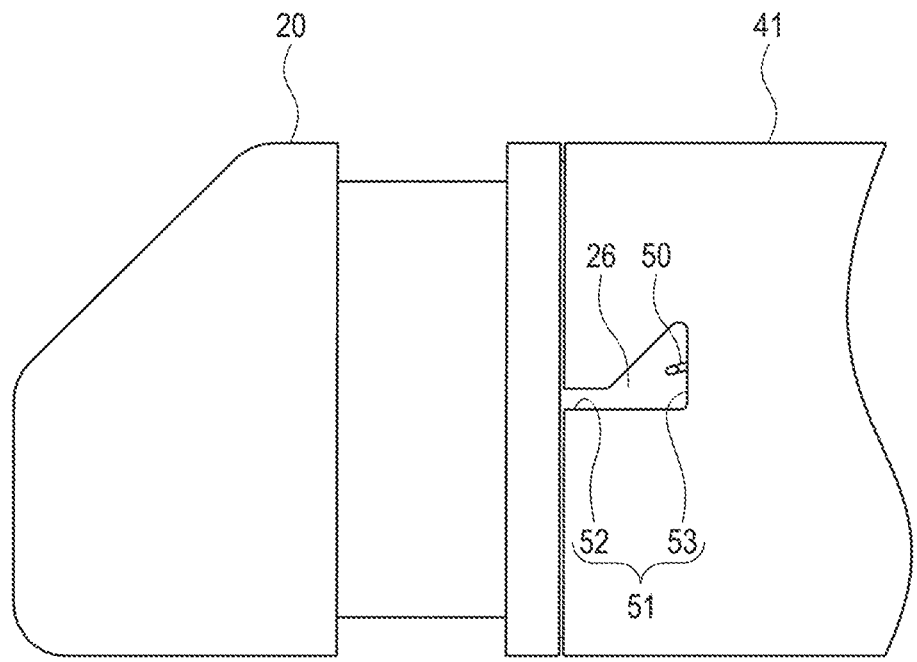
FIG. 13 relates to a third modification of the endoscope according to the one aspect of the present invention and is a side view illustrating the distal end rigid portion fitted in the most distal end bending piece to describe a shape of the opening.

As illustrated in FIG. 13, the conductive part cut portion 53 of the opening 51 formed in the bending piece 41 may be a hole with an asymmetrical shape with respect to the groove portion 52 as long as the cutting tool 100 can cut the jumper wire 50.

Fourth Modification

Figure 14:
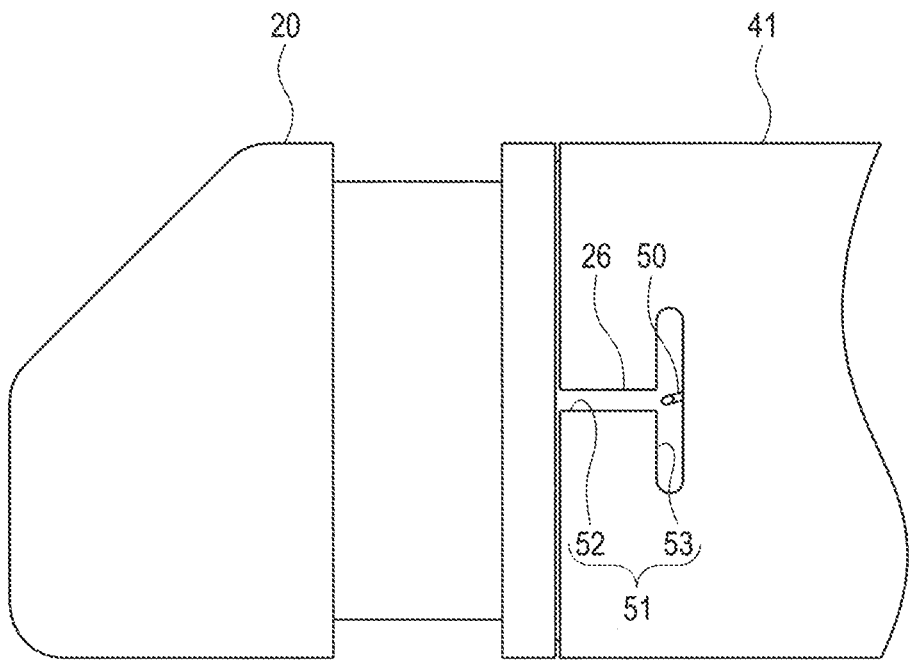
FIG. 14 relates to a fourth modification of the endoscope according to the one aspect of the present invention and is a side view illustrating the distal end rigid portion fitted in the most distal end bending piece to describe a shape of the opening.

As illustrated in FIG. 14, the opening 51 formed in the bending piece 41 may be T-shaped in which the conductive part cut portion 53 has a long-hole shape orthogonal to the groove portion 52. This makes it possible to reduce the area of the opening 51 and prevent reduction in strength of the bending piece 41.

Fifth Modification

Figure 15:
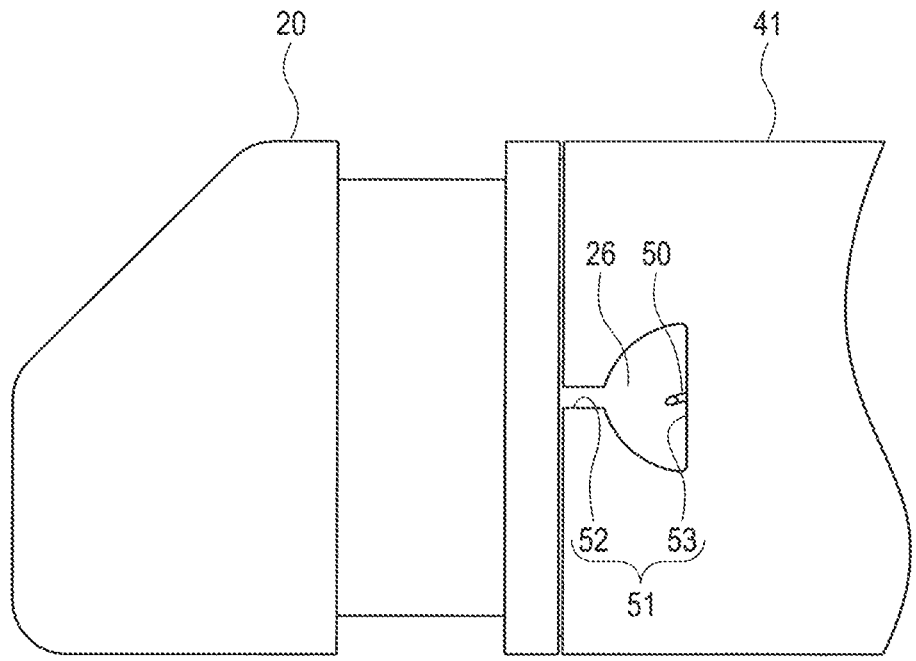
FIG. 15 relates to a fifth modification of the endoscope according to the one aspect of the present invention and is a side view illustrating the distal end rigid portion fitted in the most distal end bending piece to describe a shape of the opening.
Figure 16:
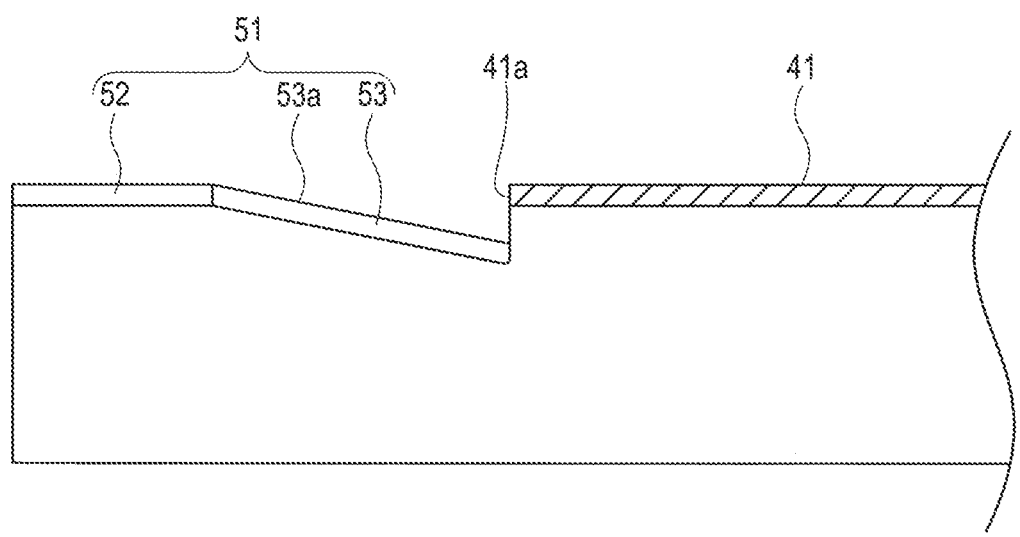
FIG. 16 relates to the fifth modification of the endoscope according to the one aspect of the present invention and is a side view illustrating the most distal end bending piece to describe a shape of the opening.

As illustrated in FIG. 15, two sides of the conductive part cut portion 53 of the opening 51 formed in the bending piece 41 that communicate with the groove portion 52 according to a curvature of the annular bending piece 41 may be arc-shaped and a slope 53a along which the cutting tool 100 is guided may be linear to facilitate cutting of the jumper wire 50 as illustrated in FIG. 16.

Sixth Modification

Figure 17:
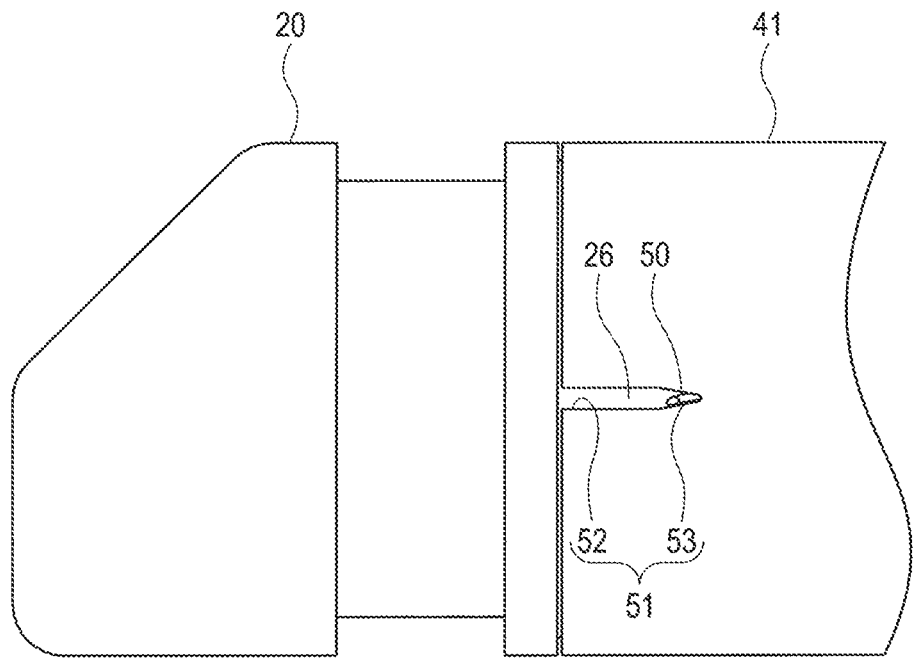
FIG. 17 relates to a sixth modification of the endoscope according to the one aspect of the present invention and is a side view illustrating the distal end rigid portion fitted in the most distal end bending piece to describe a shape of the opening.

As illustrated in FIG. 17, the conductive part cut portion 53 of the opening 51 formed in the bending piece 41 may be made thinner toward the proximal end and may be tapered in a proximal end direction to make it easier to determine the position to cut the jumper wire 50 and make it harder for the jumper wire 50 to come off.

Seventh Modification

Figure 18:
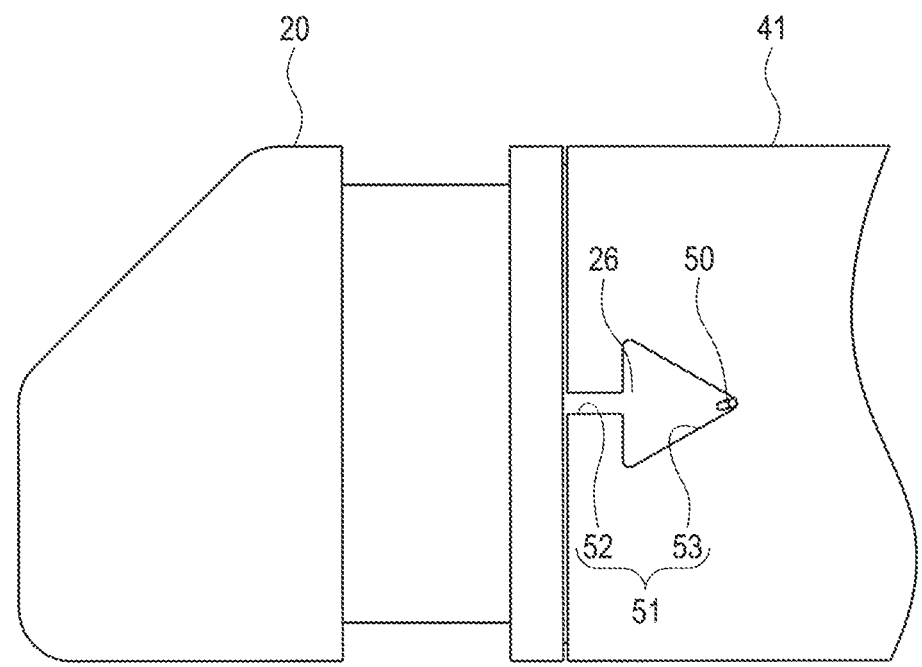
FIG. 18 relates to a seventh modification of the endoscope according to the one aspect of the present invention and is a side view illustrating the distal end rigid portion fitted in the most distal end bending piece to describe a shape of the opening.

As illustrated in FIG. 18, the opening 51 formed in the bending piece 41 may be an arrow shape with the triangular conductive part cut portion 53 reversed. It is easier to determine the position to cut the jumper wire 50 and make it harder for the jumper wire 50 to come off here, too.

Eighth Modification

Figure 19:
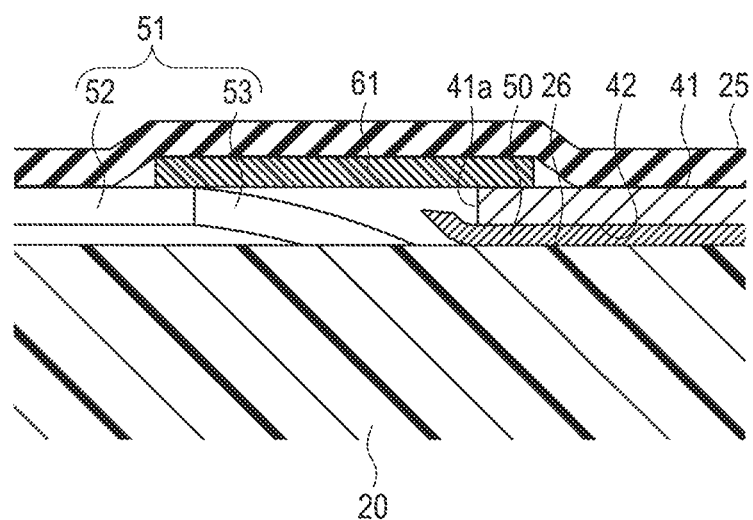
FIG. 19 relates to an eighth modification of the endoscope according to the one aspect of the present invention and is a partial cross-sectional view illustrating the distal end rigid portion provided with a covering portion to cover the opening and covered with bent rubber, and the most distal end bending piece.

As illustrated in FIG. 19, to avoid the jumper wire 50 from damaging the curved rubber 25, a covering portion 61 may be provided so as to close the opening 51 formed in the bending piece 41.

Ninth Modification

Figure 20:
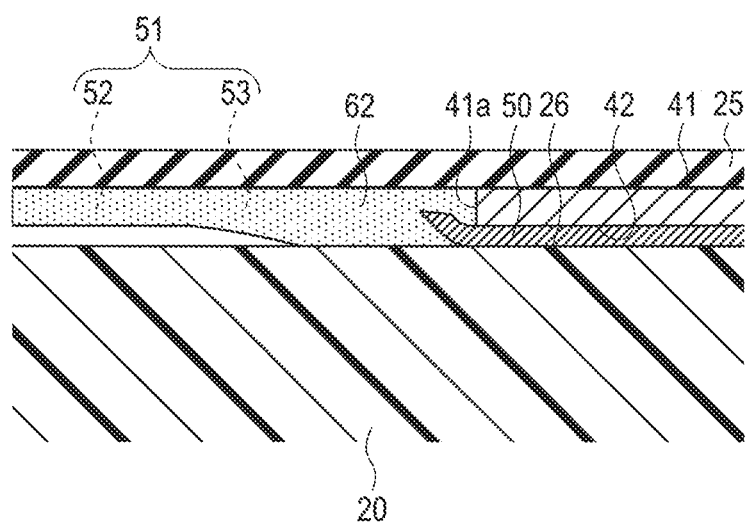
FIG. 20 relates to a ninth modification of the endoscope according to the one aspect of the present invention and is a partial cross-sectional view illustrating the distal end rigid portion, the opening of which is filled with a filler, and covered with bent rubber, and the most distal end bending piece.

As illustrated in FIG. 20, to avoid the jumper wire 50 from damaging the curved rubber 25, the opening 51 formed in the bending piece 41 may be filled with a filler 62 such as an adhesive to cover the jumper wire 50.

Tenth Modification

Figure 21:
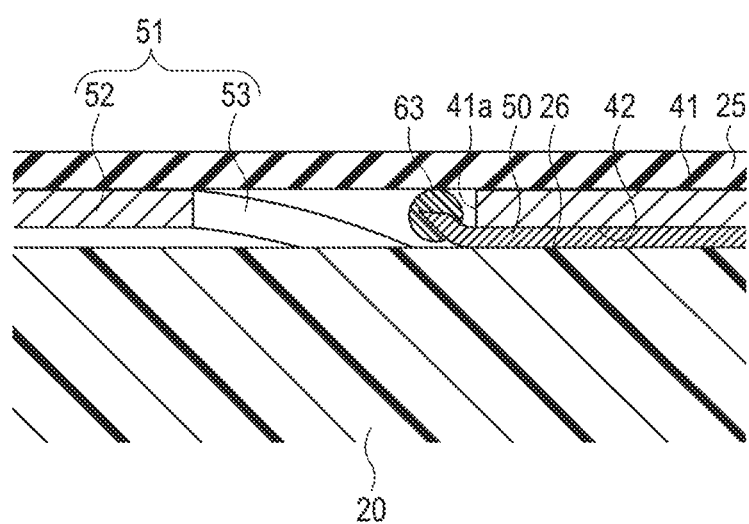
FIG. 21 relates to a tenth modification of the endoscope according to the one aspect of the present invention and is a partial cross-sectional view illustrating a protective portion provided at an end portion of the jumper wire, the distal end rigid portion covered with bent rubber and the most distal end bending piece.

As illustrated in FIG. 21, to prevent the jumper wire 50 from damaging the curved rubber 25, a protective portion 63 may be provided to cover the end portion of the jumper wire 50 exposed in the opening 51 formed in the bending piece 41.

Eleventh Modification

Figure 22:
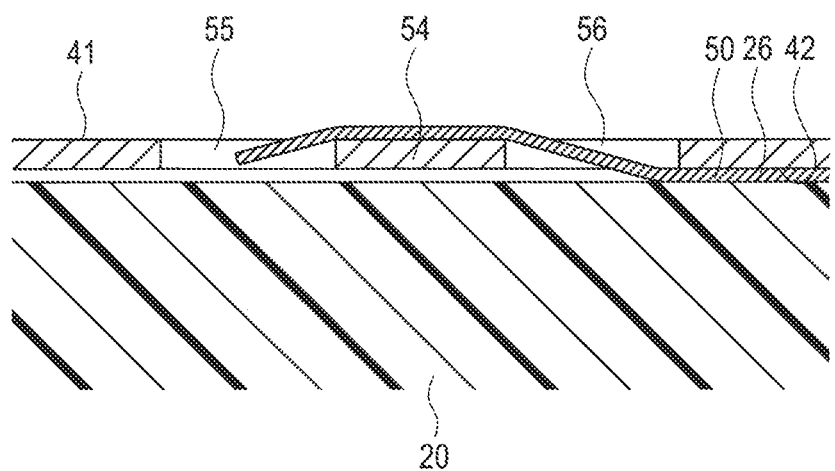
FIG. 22 relates to an eleventh modification of the endoscope according to the one aspect of the present invention and is a partial cross-sectional view illustrating the distal end rigid portion and the most distal end bending piece to describe a state in which the jumper wire is folded.

As illustrated in FIG. 22, two openings 55 and 56 may be formed in the bending piece 41, the jumper wire 50 may be made to extend out of the one opening, the end portion of the jumper wire 50 may be accommodated in the other opening 55 from outside of the outer peripheral portion 54 of the bending piece 41 between the openings 55 and 56.

Twelfth Modification

Figure 23:
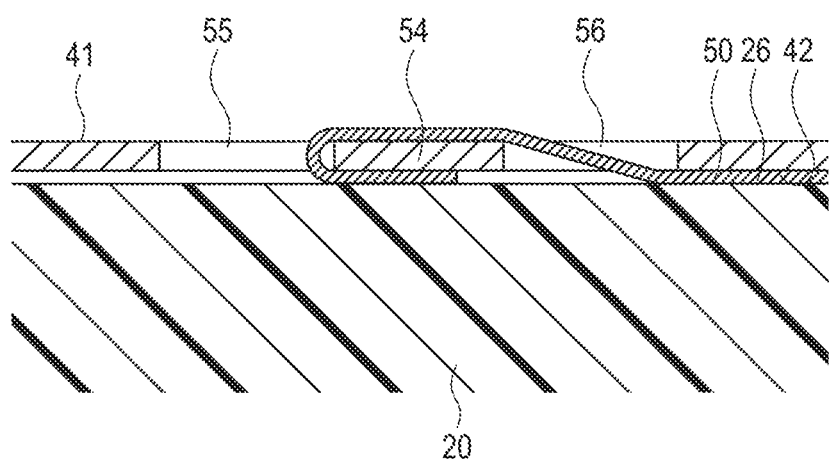
FIG. 23 relates to a twelfth modification of the endoscope according to the one aspect of the present invention and is a partial cross-sectional view illustrating the distal end rigid portion and the most distal end bending piece to describe a state in which the jumper wire is folded.

As illustrated in FIG. 23, two openings 55 and 56 may be formed in the bending piece 41, the jumper wire 50 may be made to extend out of the one opening, the end portion of the jumper wire 50 may be folded from the outside of the outer peripheral portion 54 between the openings 55 and 56 so as to sandwich the end portion of the jumper wire 50 from the other opening 55 between the outer peripheral portion 54 of the bending piece 41 and the distal end rigid portion 20.

Thirteenth Modification

Figure 24:
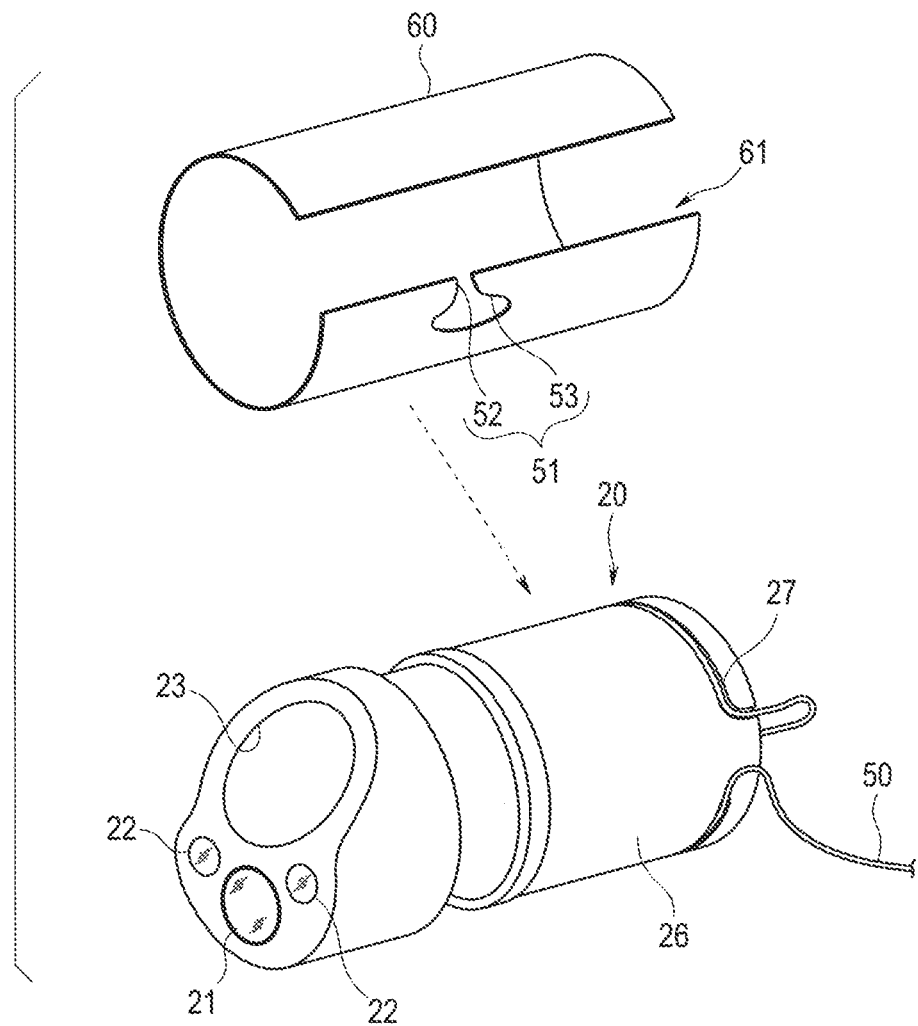
FIG. 24 relates to a thirteenth modification of the endoscope according to the one aspect of the present invention and is an exploded perspective view illustrating the distal end rigid portion fitted in a C cross section cut pipe.

As illustrated in FIG. 24, the exterior member with conductivity to be externally fitted to the outer peripheral portion 26 on the proximal end side of the distal end rigid portion 20 may be a C cross section cut tube 60. The C cross section cut tube 60 is a tubular member having a C-shaped cross section in which a clearance 61 is formed by a notch in a longitudinal direction.

In the C cross section cut tube 60, a groove portion 52 is formed in a circumferential direction from the middle of the clearance 61 and a triangular conductive part cut portion 53 is formed.

With the clearance 61 expanded, the C cross section cut tube 60 is externally fitted over the outer peripheral portion 26 on the proximal end side of the distal end rigid portion 20 in a left-right direction. Note that the C cross section cut tube 60 is attached to the distal end rigid portion 20, for example, in a snap-fit structure.

Here, the concave portion 27 in which the jumper wire 50 is disposed is formed on the outer peripheral portion 26 of the distal end rigid portion 20 in the circumferential direction orthogonal to the longitudinal direction.

Figure 25:
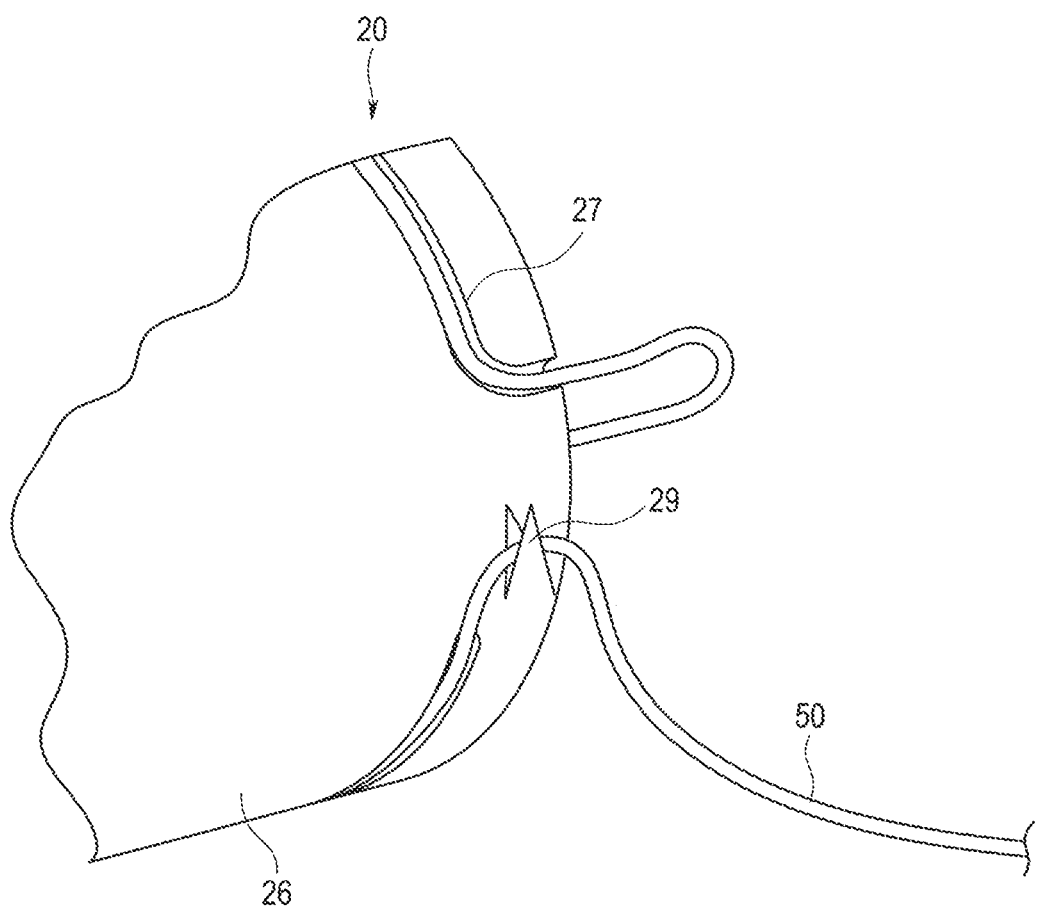
FIG. 25 relates to the thirteenth modification of the endoscope according to the one aspect of the present invention and is a partial perspective view illustrating a configuration of a notch for holding the jumper wire formed on an outer peripheral portion of the distal end rigid portion.

Note that as illustrated in FIG. 25, a notch 29 to hold the jumper wire 50 may be provided on the outer peripheral portion 26 of the distal end rigid portion 20. The notch 29 may be formed so as to be connected to the concave portion 27.

Fourteenth Modification

Figure 26:
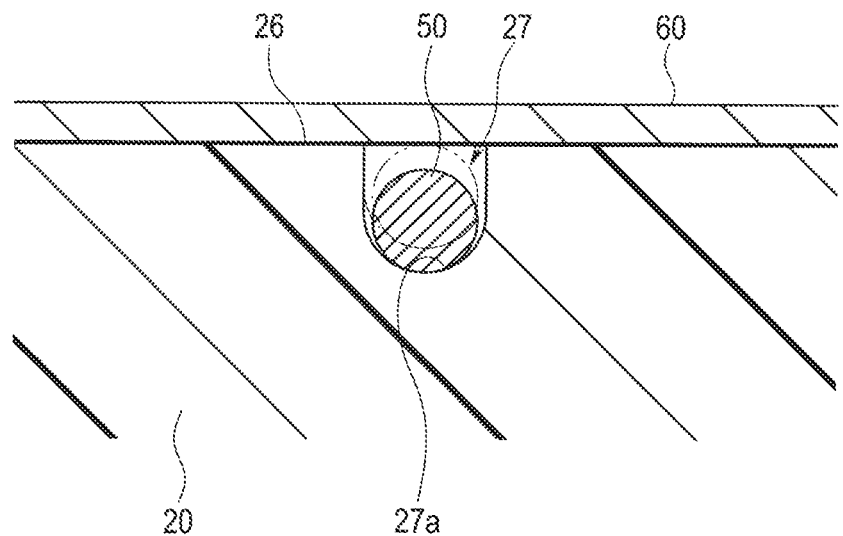
FIG. 26 relates to a fourteenth modification of the endoscope according to the one aspect of the present invention and is a partial cross-sectional view illustrating a configuration of a concave portion formed on the outer peripheral portion of the distal end rigid portion.

As illustrated in FIG. 26, the concave portion 27 may be formed so that the distance between a bottom portion 27a with U-shaped grooved cross section and an outer surface of the outer peripheral portion 26 in the longitudinal direction of the outer peripheral portion 26 of the distal end rigid portion 20 becomes shorter. Note that the concave portion 27 may be formed so that the distance between a bottom portion 27a and the outer surface of the outer peripheral portion 26 in the circumferential direction of the outer peripheral portion 26 of the distal end rigid portion 20 becomes shorter.

With the concave portion 27 formed as such, the area of contact between the jumper wire 50 and the distal end rigid portion 20 can be increased, and so the force to sandwich the jumper wire between the distal end rigid portion 20 and the bending piece 41 is dispersed compared to the case where the concave portion 27 is not formed in such a way, and it is possible to prevent the jumper wire from being cut at an unexpected position.

Figure 27:
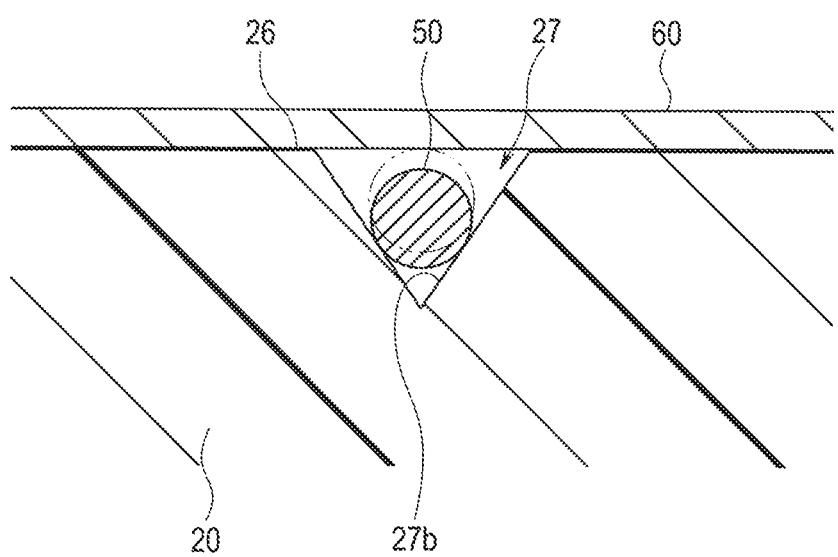
FIG. 27 relates to the fourteenth modification of the endoscope according to the one aspect of the present invention and is a partial cross-sectional view illustrating a concave portion having a configuration of V-shaped groove formed on the outer peripheral portion of the distal end rigid portion.
Figure 28:
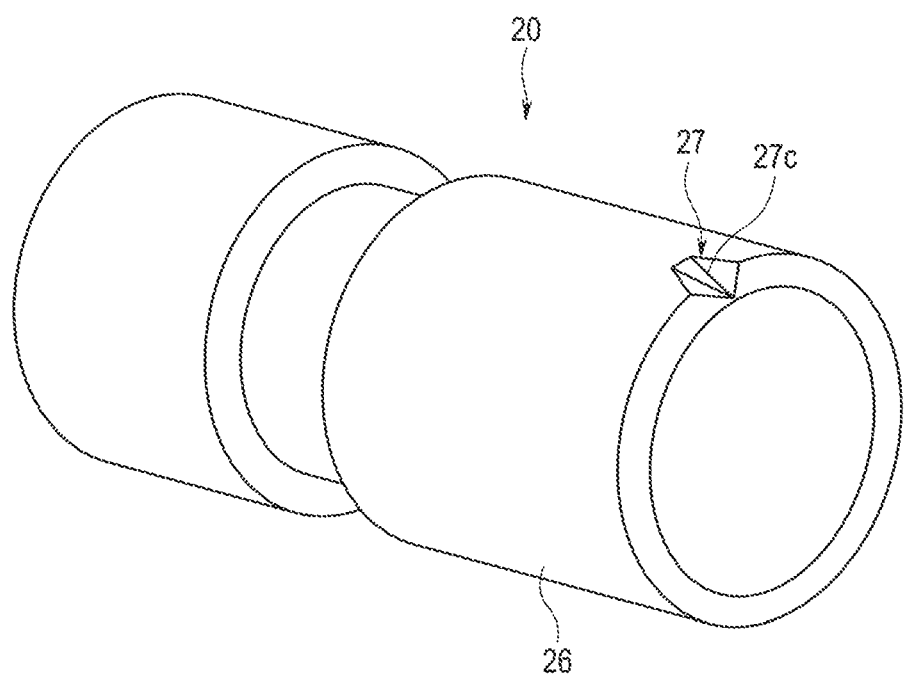
FIG. 28 relates to the fourteenth modification of the endoscope according to the one aspect of the present invention and is a perspective view illustrating a configuration of a conical concave portion formed on the outer peripheral portion of the distal end rigid portion.

Furthermore, as illustrated in FIG. 27, the concave portion 27 may be formed into a groove with V-shaped cross section so that the distance between a bottom portion 27b and the outer surface of the outer peripheral portion 26. Note that as illustrated in FIG. 28, the concave portion 27 may be formed into a conical shape in which the distance between a triangular bottom portion 27c and the outer surface of the outer peripheral portion 26 becomes shorter and at least part, a proximal end here, is V-shaped.

Since the jumper wire 50 is guided along the V shape of the concave portion 27 in this way, it is possible to prevent the position of the jumper wire 50 from shifting with respect to the distal end rigid portion 20 during assembly and carry out assembly reliably.

The inventions described in the above embodiments and modifications are not limited to the above embodiments and modifications, but various modifications can be made without departing from the spirit and scope of the invention in the implementation phase. Furthermore, the above embodiments and modifications include inventions in various phases and various inventions can be extracted according to appropriate combinations in a plurality of disclosed configuration requirements.

For instance, even when some configuration requirements are deleted from all the configuration requirements illustrated in the embodiments and modifications, configurations from which these configuration requirements are deleted can be extracted as inventions as long as the described problems can be solved and the described effects can be achieved.

What is claimed is:

1. An endoscope comprising:
   a first member provided at a distal end portion of an insertion portion;
   a conductive second member fitted to an outer circumferential surface of the first member, the second member having a circumferential opening exposing a portion of the outer circumferential surface of the first member;
   a conductive lens frame for holding one or more optical lenses, the lens frame disposed at an interior of the first member;
   a wire having a first end connected to the lens frame and a second end, a portion of the wire adjacent to the second end is sandwiched between the outer circumferential surface of the first member and an inner surface of the second member to electrically connect the lens frame and the second member.

2. The endoscope according to claim 1, wherein the first member is an electrical insulator.

3. The endoscope according to claim 1, wherein the second member accommodates, in the opening, the second end of the wire.

4. The endoscope according to claim 3, wherein the second end is accommodated closer to the first member than an outer circumferential surface of the second member.

5. The endoscope according to claim 3, wherein the opening comprises a first portion having a surface, against which the wire is cut using a cutting tool to form the second end.

6. The endoscope according to claim 5, wherein the opening comprises a second portion extending from an end of the second member and communicating with the first portion.

7. The endoscope according to claim 6, wherein a length of the first portion in a direction orthogonal to the second portion is set so that a blade of the cutting tool may be fitted within a thickness of the second member in the opening.

8. The endoscope according to claim 3, further comprising a cover configured to close the opening.

9. The endoscope according to claim 3, further comprising a protective member configured to cover the second end.

10. The endoscope according to claim 1, wherein the first member comprises a concavity in which the wire is disposed.

11. The endoscope according to claim 10, wherein the concavity is formed on an outer circumferential surface of the first member and extends in a longitudinal direction of the first member.

12. The endoscope according to claim 11, wherein a distance between a bottom of the concavity and the outer circumferential surface of the first member becomes shorter in the longitudinal direction.

13. The endoscope according to claim 11, wherein the concavity is a V-shaped groove.

14. The endoscope according to claim 1, wherein
   the opening comprises a first portion and a second portion,
   the second portion extending from an end of the second member and communicating with the first portion,
   the first portion having a width in a circumferential direction wider than a width of the second portion in the circumferential direction.

15. The endoscope according to claim 1, wherein the second end of the wire is exposed in the opening.

16. The endoscope according to claim 15, wherein the second end of the wire is located within a thickness of the second member, the thickness being in a radial direction.

17. The endoscope according to claim 1, wherein a part of the wire is located on an inner surface of the first member and on a proximal end of the first member.

18. The endoscope according to claim 1, wherein the second end of the wire is located within a thickness of the second member, the thickness being in a radial direction.

19. The endoscope according to claim 1, wherein the circumferential opening is arranged on an outer circumferential surface of the second member.

20. The endoscope according to claim 1, wherein
   the circumferential opening accommodates the second end of the wire; and
   the circumferential opening penetrates between an outer surface and an inner surface of the second member.

* * * * *